(12) United States Patent
Stern et al.

(10) Patent No.: US 8,377,863 B2
(45) Date of Patent: Feb. 19, 2013

(54) PEPTIDE PHARMACEUTICAL FOR ORAL DELIVERY

(75) Inventors: William Stern, Tenafly, NJ (US); Angelo P. Consalvo, Monroe, NY (US)

(73) Assignee: Unigene Laboratories Inc., Boonton, NJ (US)

(*) Notice: Subject to any disclaimer, the term of this patent is extended or adjusted under 35 U.S.C. 154(b) by 714 days.

(21) Appl. No.: 12/128,210

(22) Filed: May 28, 2008

(65) Prior Publication Data
US 2009/0317462 A1 Dec. 24, 2009

Related U.S. Application Data

(60) Provisional application No. 60/940,598, filed on May 29, 2007.

(51) Int. Cl.
*A61K 38/00* (2006.01)
*A61K 47/12* (2006.01)
(52) U.S. Cl. ............. 514/1.1; 424/465; 562/400
(58) Field of Classification Search .......... 514/1.1; 424/465; 562/584
See application file for complete search history.

(56) References Cited

U.S. PATENT DOCUMENTS

| | | | | |
|---|---|---|---|---|
| 4,708,934 | A | 11/1987 | Gilligan et al. | 435/68 |
| 4,849,227 | A * | 7/1989 | Cho | 424/498 |
| 5,912,014 | A | 6/1999 | Stern et al. | 424/474 |
| 5,929,027 | A * | 7/1999 | Takama et al. | 514/11.9 |
| 6,086,918 | A | 7/2000 | Stern | 424/474 |
| 6,440,392 | B1 | 8/2002 | Stern | 424/434 |
| 6,673,574 | B2 | 1/2004 | Stern et al. | 435/69.7 |
| 7,316,819 | B2 | 1/2008 | Crotts et al. | 424/464 |
| RE40,812 | E | 6/2009 | Stern | 424/434 |
| 2001/0055648 | A1 * | 12/2001 | Lee et al. | 427/213 |
| 2003/0017203 | A1 | 1/2003 | Crotts et al. | |
| 2004/0197323 | A1 | 10/2004 | Mehta et al. | 424/130.1 |
| 2005/0123507 | A1 | 6/2005 | Ameri et al. | 424/85.1 |
| 2005/0282756 | A1 | 12/2005 | Mehta et al. | |
| 2006/0127995 | A1 | 6/2006 | Consalvo et al. | 435/128 |
| 2006/0270603 | A1 | 11/2006 | Mehta et al. | |
| 2006/0292672 | A1 | 12/2006 | Miller et al. | 435/69.1 |

FOREIGN PATENT DOCUMENTS

| | | |
|---|---|---|
| CA | 2 070 061 | 2/2004 |
| EP | 0308067 | 3/1989 |
| EP | 0382403 | 8/1990 |
| EP | 0 517 211 A1 | 12/1992 |
| WO | 97/33531 A1 | 9/1997 |
| WO | 2004/064758 A2 | 8/2004 |

OTHER PUBLICATIONS

Mehta, Nozer M., BioPharm International, (Jul. 2004) vol. 17, No. 7, pp. 44-46.*
International Search Report and Written Opinion dated Aug. 15, 2008 issued in corresponding PCT Application No. PCT/US08/06804.
Ray et al., 2002, Protein Expression and Purification, 26:249-259.
Biotechnology, vol. 11 (1993) pp. 64-70.
International Preliminary Report on Patentability dated Dec. 10, 2009 corresponding to International Patent Application No. PCT/US2008/006804.
Canadian Office Action dated Feb. 15, 2010 in corresponding Canadian Patent Application No. 2,631,841 (English language).
Nozer M. Mehta, "Oral Delivery and Recombinant Production of Peptide Hormones Part II: Recombinant Production of Therapeutic Peptides", Biopharm International, pp. 44-46, www.biopharm-mag.com, Jul. 2004.

* cited by examiner

*Primary Examiner* — David Lukton
(74) *Attorney, Agent, or Firm* — Greenberg Traurig, LLP; David J. Dykeman; Danielle T. Abramson

(57) ABSTRACT

Acid-containing oral pharmaceutical compositions are provided wherein the pharmaceutical active agents are peptide compounds (i.e., those that include a plurality of amino acids and at least one peptide bond in their molecular structures). Certain barrier layers and/or particulate coated acid are used to reduce any adverse interactions that might otherwise occur between the acid of the compositions and other components of the composition. Use of these barrier layers and/or use of particulate coated acid is believed to promote a more simultaneous release of the components of the composition than is achieved by prior art acid-protection techniques, thus enhancing, and making more consistent, the bioavailability of the active peptide compounds.

83 Claims, 2 Drawing Sheets

Dissolution Profiles of Tablets Made from Coated and Non-coated Citric Acid

PEPTIDE PHARMACEUTICAL FOR ORAL DELIVERY

CROSS REFERENCE TO RELATED APPLICATION(S)

This application claims priority of U.S. Provisional Application Ser. No. 60/940,598 filed May 29, 2007, the disclosure of which is incorporated by reference herein.

BACKGROUND OF THE INVENTION

1. Field of the Invention

The present invention relates to acid-containing oral peptide pharmaceutical compositions wherein the pharmaceutical active agents are peptide compounds (i.e. those that include a plurality of amino acids and at least one peptide bond in their molecular structures), and particularly to the use of certain barrier layers and/or particulate coated acid to reduce adverse interactions that might otherwise occur between the acid of the compositions and other components of the composition. Use of these barrier layers and/or use of particulate coated acid is believed to enhance stability of the composition, and following administration, to promote a more simultaneous release of the components of the composition than is achieved by prior art acid-protection techniques. This enhances, and makes more consistent, the bioavailability of the active peptide compounds.

2. Description of the Related Art

Numerous human hormones, neurotransmitters and other important biological compounds have peptides as a substantial part of their molecular structures. Many diseases respond positively to raising the level of these peptide compounds in patients. Therapeutically effective amount of such biologically relevant peptides may be administered to patients in a variety of ways. However, as discussed further below, preferred oral administration is very difficult with this type of active compound.

Salmon calcitonin, for example, is a peptide hormone which decreases uptake of calcium from bone. When used to treat bone-related diseases and calcium disorders (such as osteoporosis, Paget's disease, hypercalcemia of malignancy, and the like), it has the effect of helping maintain bone density. Many types of calcitonin have been isolated (e.g., human calcitonin, salmon calcitonin, eel calcitonin, elkatonin, porcine calcitonin, and chicken calcitonin). There is significant lack of structural homology among the various calcitonin types. For example, there is only 50% percent identity between the amino acids making up human calcitonin and those making up salmon calcitonin. Notwithstanding the difference in molecular structure, salmon calcitonin may be used in the human treatment of the calcitonin-responsive diseases discussed above.

Peptide pharmaceuticals used in the prior art frequently have been administered by injection or by nasal administration. Insulin, for example, is one of many peptide pharmaceuticals frequently administered by injection. A more preferred oral administration tends to be problematic because peptide active compounds are very susceptible to degradation in the stomach and intestines. Salmon calcitonin, for example, lacks sufficient stability in the gastrointestinal tract, and tends to be poorly transported through intestinal walls into the blood. However, injection and nasal administration are significantly less convenient than, and involve more patient discomfort than, oral administration. Often this inconvenience or discomfort results in substantial patient noncompliance with a treatment regimen. Thus, there is a need in the art for more effective and reproducible oral administration of peptide pharmaceuticals.

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Specific difficulties arising from the oral administration of a peptide like salmon calcitonin and other peptides discussed herein involve the relatively large size of the molecule, and the charge distribution it carries. This may make it more difficult for the peptide to penetrate the mucus along intestinal walls or to cross the intestinal brush border membrane into the blood. These additional problems may further contribute to limited bioavailability.

In U.S. Pat. No. 6,086,918 (Stern et al), peptides were delivered orally using a multi-component system which included, inter alia, significant quantities of acid useful in lowering intestinal pH and hence the activity of intestinal proteases that have neutral or basic pH optima. For best results in prior art pharmaceuticals of this type, it is preferred that the several components of the system be released into the intestines as close to simultaneously as possible. Uniform dispersion of the many components of the composition can aid this objective. However, interaction of the acid with the peptide active agent is preferably avoided, and prior art attempts to reduce interaction between acid and peptide active agent frequently resulted in less uniform dispersion of the various components or otherwise tended to make release of all components less simultaneous. This, in turn, harmed peptide bioavailability, as well as consistency of that bioavailability from one administration to the next, either in the same subject or from one subject to the next.

U.S. Patent Publication No. 2003/0017203 (Crotts et al) discloses a water-soluble coating that substantially prevents contact between a pH-lowering agent in a pharmaceutical formulation and an outer enteric coating. That publication, however, discloses a laminate structure wherein active peptide and an absorption enhancer are in one layer of the laminate, while acid is in another. This desirably helps reduce interaction of peptide with pharmaceutical acid, and interaction of absorption enhancer with pharmaceutical acid, but makes consistent, reproducible, and near-simultaneous release of all components more difficult. Acid can also interact unfavorably with other components of the pharmaceutical composition. A bilayer structure, however, provides physical separation of components whose complexity may result in a undesirable variability in dissolution that the present invention seeks to reduce.

Prior art acid-containing oral peptide pharmaceuticals frequently used enteric coatings to separate peptide active agents from stomach proteases. Enteric coating does not dissolve in the acid environment of the stomach, but dissolves readily in the basic environment of the intestines, thus desirably targeting an intestinal release. Another problem caused by the significant acid levels of prior art acid-containing oral peptide pharmaceuticals is slower or uneven dissolution of the enteric coating in the intestines. This is believed to be because the high acid content of the composition can interfere with the desirable quick dissolution of the enteric coating by creating localized acid environment (in which enteric coating does not dissolve) even in the generally basic environment of the intestines. As noted above however, prior art attempts to avoid interaction between acid and other components of the pharmaceutical composition have themselves had undesirable effects on the simultaneity of release of the various pharmaceutical components. Variability of dissolution may undesirably contribute to variability of bioavailability.

There is therefore a need in the art for acid-containing oral peptide pharmaceutical compositions wherein the interactions between acid and other components can be minimized, while still maintaining good near-simultaneous release of the various components.

SUMMARY OF THE INVENTION

It is accordingly an object of the present invention to better prevent undesirable effects of acid on peptide active agents and/or enteric coatings while maintaining good dissolution profiles wherein all ingredients of the oral pharmaceutical composition are released into the intestines in close time proximity, thus enhancing bioavailability.

It is a further object to provide a therapeutically effective oral pharmaceutical composition for reliably and consistently delivering pharmaceutical peptides when administered orally.

It is a further object of the invention to provide therapeutic oral compositions containing peptide active agents having good and consistent bioavailability.

In one embodiment, the invention provides a pharmaceutical composition for oral delivery of a physiologically active peptide agent comprising:

(A) said peptide agent;
(B) at least one pharmaceutically acceptable acid wherein said acid is present in said pharmaceutical composition in a quantity which, if said composition were added to 10 milliliters of 0.1M aqueous sodium bicarbonate solution, would be sufficient to lower the pH of said solution to no higher than 5.5;
(C) an acid-resistant protective vehicle (e.g., enteric coating) effective to transport said pharmaceutical composition through the stomach of a patient while preventing contact between said active peptide agent and stomach proteases; and
(D) a water soluble barrier layer that separates said acid from said protective vehicle;
wherein either (a) said barrier layer adds 3-6% to the weight of the pharmaceutical composition, exclusive of any acid-resistant protective vehicle, or (b) said barrier layer comprises a material having water solubility in excess of 11 grams per 100 milliliters of water at room temperature, or (c) said peptide agent and said acid are in the same or only layer of said composition.

In another embodiment, the invention provides a pharmaceutical composition for oral delivery of a physiologically active peptide agent comprising said active peptide agent, and pharmaceutically acceptable acid particles that are coated with a pharmaceutically acceptable protective coating that is non-acidic and has a solubility in water of at least one gram per 100 milliliters of water at room temperature; wherein total acid in said pharmaceutical composition is in a quantity which, if said composition were added to ten milliliters of 0.1M aqueous sodium bicarbonate solution, would be sufficient to lower the pH of said solution to no higher than 5.5.

In another embodiment, the invention provides a pharmaceutical composition for oral delivery of a physiologically active peptide agent comprising:

(A) said peptide agent;
(B) at least one pharmaceutically acceptable acid wherein said acid is present in said pharmaceutical composition in a quantity which, if said composition were added to 10 milliliters of 0.1M aqueous sodium bicarbonate solution, would be sufficient to lower the pH of said solution to no higher than 5.5, wherein said acid comprises acid particles that are coated with a pharmaceutically acceptable protective coating that is non-acidic and has a solubility in water of at least one gram per 100 milliliters of water at room temperature;
(C) an acid resistant protective vehicle effective to transport said pharmaceutical composition through the stomach of a patient while preventing contact between said active peptide agent and stomach proteases; and
(D) a water soluble barrier layer that separates said coated acid from said protective vehicle;
wherein either (a) said barrier layer adds at least 3% to the weight of the pharmaceutical composition, exclusive of any acid-protective vehicle, or (b) said barrier layer comprises a material having water solubility in excess of one gram per 100 milliliters of water at room temperature, or (c) said peptide agent and said acid are in the same or only layer of said composition.

Without intending to be bound by theory, it is believed that, when the pharmaceutical composition of the invention is administered to subjects, significant quantities of acid are released by the composition in close time proximity with release of the peptide active agent. This reduces the activity of neutral to basic-acting proteases (e.g. luminal or digestive protease and proteases of the brush border membrane) by lowering pH below the optimal activity range of these proteases. Thus, the peptide active agents are less vulnerable to proteolytic degradation until they can be successfully transported into the bloodstream. Without intending to be bound by theory, it is believed that the materials and structures of the pharmaceutical compositions herein reduce adverse interactions between the acid of the compositions and the other components of the composition. It is further believed that the inventions herein promote a more simultaneous release of the components of the composition than is achieved by prior art acid-protection techniques, thus enhancing, and making more consistent, the bioavailability of the active peptide compounds.

The pharmaceutical compositions of the invention have both human and veterinary applications. Any animal having neutral to basic-acting proteases in the digestive tract should benefit from the invention's more-simultaneous release of significant quantities of acid together with the peptide active agent.

Other features and advantages of the present invention will become apparent from the following detailed, and non-limiting, description of certain preferred embodiments.

BRIEF DESCRIPTION OF THE DRAWINGS

FIG. 2 is not necessarily to scale, and is only for the purpose of illustrating preferred relative locations of various layers. The preferred percentages of material used in the various layers are discussed elsewhere herein.

DETAILED DESCRIPTION OF PREFERRED EMBODIMENTS OF THE INVENTION

Figure 1:
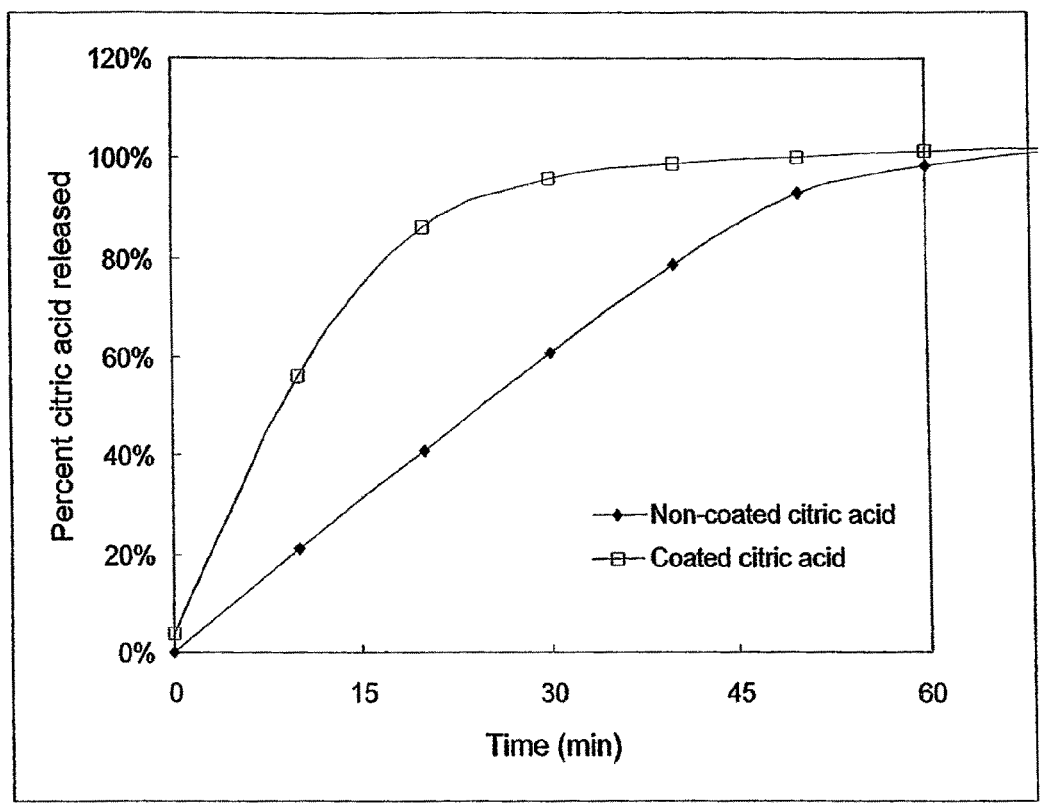
FIG. 1 is a comparison of the dissolution profiles of pharmaceutical tablets containing coated acid particles versus uncoated acid.

The present invention includes use of significant quantities of acid to improve bioavailability of peptide pharmaceutical active agents as taught in U.S. Pat. No. 6,086,918, the entire disclosure of which is incorporated by reference herein.

In accordance with the invention, patients in need of treatment with peptide active ingredients are provided with an oral pharmaceutical composition thereof (at appropriate dosage), preferably but not necessarily in tablet or capsule form of an ordinary size in the pharmaceutical industry. The dosages and frequency of administering the products are discussed in more detail below. Patients who may benefit are any who suffer from disorders that respond favorably to increased levels of a peptide-containing compound. For example, oral salmon calcitonin in accordance with the invention may be used to treat patients who suffer from calcium disorders or bone diseases. The invention may be used, for example, to treat osteoporosis, Paget's disease, hypercalcemia of malignancy and the like, with oral calcitonin, preferably salmon calcitonin.

Salmon calcitonin is a preferred active ingredient for use in accordance with the invention for a number of reasons. For example, it provides a number of advantages over even human calcitonin, even when used as a pharmaceutical agent for human patients. Among the advantages provided by utilizing salmon calcitonin instead of human calcitonin for the treatment of human osteoporosis are increased potency, analgesia and increased half-life. Also, lower dosages are necessary than with human calcitonin. There is substantial non-homology between salmon and human calcitonin, with only 50% identity in the amino acid sequences of the two calcitonins. Notwithstanding the foregoing preference for salmon calcitonin, other calcitonins and other peptides (discussed in more detail, infra) may be used in accordance with the invention.

Because the oral delivery provided by the pharmaceuticals herein enhances protection of the peptide active agents from proteolytic degradation, it is expected to increase bioavailability of a wide range of therapeutic peptide active agents that would otherwise be more prone to proteolytic degradation. A separate section below discusses the various peptide active agents.

Not all embodiments of the invention include an acid protective vehicle such as an outer layer of enteric coating. Such vehicles are desirable for enhancing bioavailability, but can slow uptake of the active ingredients into the bloodstream. Thus, in time-sensitive medical applications, for example, pain relief, there can be some advantage in sacrificing some bioavailability in return for faster delivery in the bloodstream. For use in medical applications where bioavailability is deemed more important than speed, use of an acid protective vehicle is preferred.

In embodiments that utilize an acid protective vehicle, quick and uniform dissolution of that vehicle in the intestines may be facilitated by keeping the acid of the composition away from said vehicle during its dissolution. This may be accomplished in accordance with the invention in one of two ways (or in certain preferred embodiments by utilizing both techniques). First, the use of a protective barrier layer between the acid protective vehicle and the acid of the pharmaceutical composition can enhance the more simultaneous release of all pharmaceutical composition in the intestines by permitting most of the enteric coating to dissolve in the intestines before the acid of the pharmaceutical composition is released or otherwise comes in contact with the acid protective vehicle. Otherwise the acid could adversely affect the dissolution of the protective vehicle (which is insoluble in acid environment). This barrier layer is expected to provide this benefit regardless of the form in which the acid is supplied, and even when coated acid particles (used in other embodiments of the invention) are not present. Details regarding preferred materials and thicknesses for the protective barrier layer are discussed infra in a section directed to this layer.

Alternatively, the acid of the composition may be provided in the form of coated acid particles. The coating on these particles is a pharmaceutically acceptable protective coating that is non-acidic and has a solubility in water of at least one gram per 100 milliliters of water at room temperature. In addition to desirably separating the pharmaceutical acid from the pharmaceutical active peptide, this coating on the acid particles may help protect the pharmaceutical composition's enteric coating (or other acid protective vehicle) from the undesirable effects acid can have on quick uniform dissolution of the outer coating in the intestines. This is true even in embodiments of the invention that do not include the protective barrier layer. In some, but not all, embodiments of the invention, both (1) the protective barrier layer is present, and (2) the acid is supplied, at least in part, in the form of coated acid particles.

Likewise, providing acid to the pharmaceutical composition in the form of the foregoing coated acid particles provides numerous advantages that are independent of any effect on enteric coating, and independent of whether or not a protective barrier layer is used. Such coated acid particles may therefore be used advantageously even in embodiments of the invention that include neither outer coating of acid protective vehicle, nor protective barrier layer. In particular, acid in the form of coated particles may desirably be thoroughly intermixed with the peptide active agent, while undesirable acid-peptide interaction is minimized. Without intending to be bound by theory, this thorough intermixing is believed to facilitate simultaneous release of each component together so that acid may better protect the peptide, in the intestinal environment, by reducing peptide degradation from the activity of local proteases having neutral or basic pH optima.

In some but not all embodiments, an absorption enhancer, as described in more detail in a separate section, infra, is included in the pharmaceutical composition to further enhance bioavailability. In one preferred embodiment, coated acid particles, peptide active agent, absorption enhancer, acid protective vehicle and protective barrier layer are all present. The use of coated acid particles, in addition to reducing undesirable acid interactions with other components discussed herein, desirably reduces acid interaction with absorption enhancer (when used) or with surfactant (when used).

Figure 2:
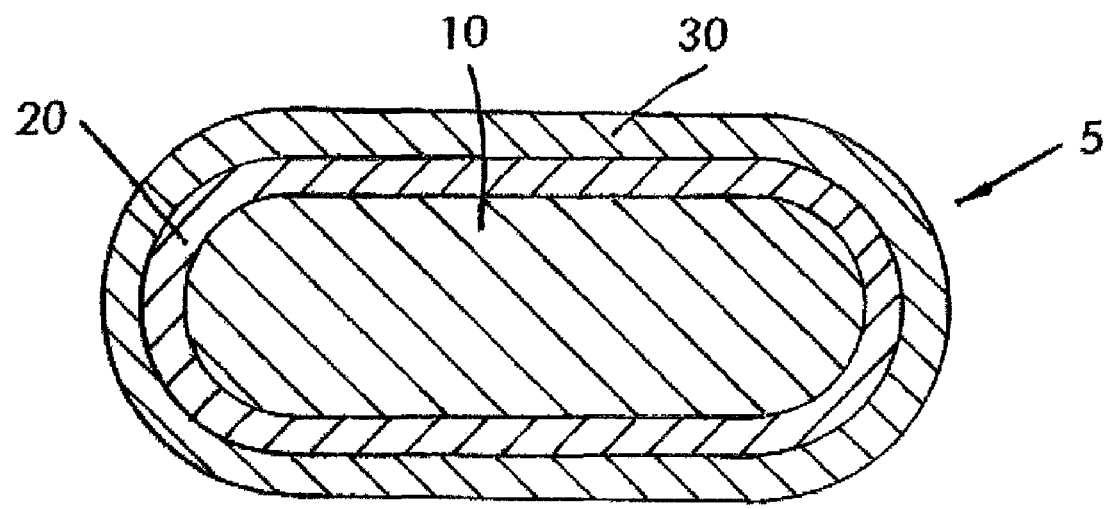
FIG. 2 is a sectional view of a pharmaceutical tablet that utilizes the embodiment of the invention relating to a protective barrier layer that can enhance dissolution of an enteric coating where enteric coatings are used. The figure shows the relative positions of the protective barrier, enteric coating and reminder of the pharmaceutical composition in one preferred embodiment.

In one preferred embodiment, coated acid, peptide and, optionally, one or more of any optional components discussed herein, e.g. an absorption enhancer, are thoroughly intermixed. The mixture is then coated with both a protective barrier layer and an outer acid-protective vehicle. One version of this embodiment is illustrated by FIG. 2, a sectional view of an embodiment utilizing a pharmaceutical tablet 5. As shown in FIG. 2, a water-soluble barrier layer 20 preferably lies just inside of an acid protective vehicle layer 30, and separates vehicle layer 30 from the intermixed remaining contents 10. FIG. 2 shows the relative positions of the water-soluble barrier layer, acid-protective vehicle and remaining ingredients. FIG. 2 is not necessarily to scale, and is only for the purpose of illustrating preferred relative locations of various layers. The preferred percentages of material used in the various layers are discussed elsewhere herein.

The acid protective vehicle preferably constitutes an outermost protective layer surrounding the remainder of the pharmaceutical composition. The vehicle does not dissolve in the acidic stomach environment, thus protecting the active peptide components from stomach proteases. Without intending to be bound by theory, it is believed that, later, in the basic pH environment of the intestines, the vehicle dissolves quickly without interference from the pharmaceutical acid from which the vehicle is separated by either the barrier layer, or the coating on the acid particles, or both. It is believed that, once the protective vehicle dissolves, the water-soluble barrier layer and the coating surrounding the acid particles quickly release the remaining components of the composition in close time proximity.

The acid is believed to lower the local intestinal pH (where the active agent has been released) to levels below the optimal range for many intestinal proteases. It is believed that this decrease in pH reduces the proteolytic activity of the intestinal proteases, thus affording protection to the peptide from potential degradation. The activity of these proteases is diminished by the temporarily acidic environment provided by the invention. It is preferred that sufficient acid be provided that local intestinal pH is lowered temporarily to 5.5 or below, preferably 4.7 or below and more preferably 3.5 or below. The sodium bicarbonate test described infra (in the section captioned "the pH-Lowering Agent") is indicative of the required acid amount. Preferably, conditions of reduced intestinal pH persist for a time period sufficient to protect the peptide agent from proteolytic degradation until at least some of the peptide agent has had an opportunity to cross the intestinal wall into the bloodstream. Optionally, absorption enhancers, when used, may synergistically promote peptide absorption into the blood while conditions of reduced proteolytic activity prevail. Preferred absorption enhancers and their use are discussed in more detail in a separate section, infra.

It is important that acid and peptide (and, when present, absorption enhancer) are released together to the extent possible. The acid is then better able to protect the peptide by reducing degradation of peptide by action of neutral or basic-acting proteases until the peptide crosses the intestinal wall into the bloodstream. A near-simultaneous release of absorption enhancer (when used) can further enhance that crossing of the intestinal wall. In a preferred tablet form of the invention, additional optional materials, discussed in separate sections infra, aid in forming tablets of appropriate hardness that resist breaking prior to administration, and undergo consistent fast and complete dissolution at the appropriate time after administration. It is important that tablets or capsules resist formation of "ghosts," partially intact tablets or capsules that remain from incomplete dissolution.

The mechanism by which the invention is believed to accomplish the goal of enhanced bioavailability is aided by having active components of the pharmaceutical composition released together as simultaneously as possible. To this end, in embodiments where an acid-resistant protective vehicle is used, it is preferred to keep the volume of the acid-resistant protective vehicle as low as possible consistent with providing protection of the peptide active agent from stomach proteases. Thus, the acid-resistant protective vehicle is less likely to interfere with peptide release, or with the release of other components in close time proximity with the peptide. The acid-resistant protective vehicle should normally add less than 30% to the weight of the remainder of pharmaceutical composition (i.e., the other components of the composition excluding the acid-resistant protective vehicle). Preferably, it is less than 20% and, more preferably, the enteric coating adds between 10% and 20% to the weight of the uncoated ingredients. When a water-soluble barrier layer is used in addition to the acid-resistant protective vehicle, less acid-resistant protective vehicle may be required. In some such embodiments, a weight gain of from 4-10%, or in some embodiments 4-7% is provided by the acid-resistant protective vehicle. A water-soluble protective barrier layer between the acid protective vehicle and the pharmaceutical acid or other contents of the composition preferably adds at least a 3% weight gain to the composition. In some embodiments, it adds 3-6%. In some preferred embodiments, the amount of water-soluble barrier layer exceeds the amount of acid-protective vehicle.

In embodiments in which an absorption enhancer is optionally used, the enhancer, which may be a solubility enhancer and/or transport enhancer (as described in more detail below), aids transport of the peptide agent from the intestine to the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility desirably provides (1) a more simultaneous release of the active components of the invention into the aqueous portion of the intestine, (2) better solubility of the peptide in, and transport through, a mucous layer along the intestinal walls. Once the peptide active ingredient reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Components of preferred pharmaceutical compositions of the invention, including preferred optional components, are discussed in separate sections below. Species suggested for each component can be used alone or in combination with other species. For example, combinations of multiple pH-lowering agents, or (where an absorption enhancer is used) multiple enhancers can be used as well as using just a single pH-lowering agent and/or single enhancer. Some preferred combinations are also discussed below. One or more optional components may be included in combination with other optional components.

Peptide Active Ingredients

Peptide active ingredients which may benefit from oral delivery in accordance with the invention include any therapeutic agent that is physiologically active and has, as part of its molecular structure, a plurality of amino acids and at least one peptide bond. In preferred embodiments of the invention, degradation of the active ingredients by protease is suppressed by several mechanisms that would otherwise tend to cleave one or more of the peptide bonds of the active ingredient. In addition to natural amino acids, the amino acids may be D-amino acids or unnatural amino acids, some examples of which are discussed infra. The molecular structure may further include other substituents or modifications. For example, salmon calcitonin, a preferred peptide active agent herein, is amidated at its C-terminus. Some peptides may be amidated at locations that are not amidated in nature, or may be otherwise modified.

Peptide active compounds of the invention include, but are not limited to, insulin, vasopressin, calcitonin (including not only the preferred salmon calcitonin, but other calcitonins as well). Other examples include calcitonin gene-related peptide, parathyroid hormone (including amidated or unamidated truncates thereof such as PTH1-31-amide), desmopressin, luteinizing hormone-releasing factor, erythropoietin, tissue plasminogen activators, human growth hormone, adrenocorticototropin, various interleukins, enkephalin, and the like. Many others are known in the art. It is expected that any pharmaceutical compound having peptide bonds which would be subject to cleavage in the gastrointestinal tract would benefit from oral delivery in accordance with the present invention because of the reduction in such cleavage that is afforded by the present invention.

Both man-made and natural peptides can be orally delivered in accordance with the invention. Thus, the peptide active compound, in some embodiments, could be glucagon-like peptide-1 (GLP-1), or analogs thereof, desmopressin (DDAVP), leuprolide, 2,6-dimethyltyrosine-D-arginine-phenylalanine-lysine amide (DMT-DALDA), peptidomimetics and the like.

When salmon calcitonin is used, it preferably comprises from 0.02 to 0.2 percent by weight relative to the total weight of the overall pharmaceutical composition (exclusive of any acid-resistant protective coating). Salmon calcitonin is commercially available (for example, from BACHEM, Torrence, Calif.). Alternatively it may be synthesized by known methods, some of which are discussed briefly below. Other peptide active agents should be present at higher or lower concentrations depending on desired target blood concentrations for the active compound and its bioavailability in the oral delivery system of the invention.

When salmon calcitonin is used as an active agent, salmon calcitonin precursors may be made by either chemical or recombinant syntheses known in the art. Precursors of other amidated peptide active agents may be made in like manner. Recombinant production is believed significantly more cost effective. Precursors are converted to active salmon calcitonin by amidation reactions that are also known in the art. For example, enzymatic amidation is described in U.S. Pat. No. 4,708,934 and European Patent Publications 0 308 067 and 0 382 403. Recombinant production is preferred for both the precursor and the enzyme that catalyzes the conversion of the precursor to salmon calcitonin. Such recombinant production is discussed in Biotechnology, Vol. 11 (1993) pp. 64-70, which further describes a conversion of a precursor to an amidated product. The recombinant product reported there is identical to natural salmon calcitonin, and to salmon calcitonin produced using solution and solid phase chemical peptide synthesis. Production of salmon calcitonin or other amidated products may also be accomplished using the process and amidating enzyme set forth by Consalvo, et al in U.S. Patent Publication 2006/0127995; Miller et al, U.S. Patent Publication 2006/0292672; Ray et al, 2002, *Protein Expression and Purification*, 26:249-259; and Mehta, 2004, *Biopharm. International*, July, pp. 44-46.

The production of the preferred recombinant salmon calcitonin (rsCT) may proceed, for example, by producing glycine-extended salmon calcitonin precursor in *E. coli* as a soluble fusion protein with glutathione-S-transferase. The glycine-extended precursor has a molecular structure that is identical to active salmon calcitonin except at the C-terminal (where salmon calcitonin terminates -pro-NH$_2$, while the precursor terminates -pro-gly). An alpha-amidating enzyme described in the publications above catalyzes conversion of precursors to salmon calcitonin. That enzyme is preferably recombinantly produced, for example, in Chinese Hamster Ovary (CHO) cells), as described in the *Biotechnology* and *Biopharm.* articles cited above. Other precursors to other amidated peptides may be produced in like manner.

Peptide active agents that do not require amidation may also be produced in like manner, but without the amidation step. Some peptide active agents are commercially available. Those that are not may be produced by techniques known in the art.

The pH-Lowering Agent (Acid)

The total amount of the pH-lowering compound to be administered with each administration of salmon calcitonin should preferably be an amount which, when it is released into the intestine, is sufficient to lower the local intestinal pH substantially below the pH optima for proteases found there. The quantity required will necessarily vary with several factors including the type of pH-lowering agent used (discussed infra) and the equivalents of protons provided by a given pH-lowering agent. In practice, the amount of pH-lowering agent expected to provide good bioavailability is an amount which, if the pharmaceutical composition of the invention were added to a solution of 10 milliliters of 0.1 M sodium bicarbonate, would lower the pH of that sodium bicarbonate solution to no higher than 5.5, and preferably no higher than 4.7, most preferably no higher than 3.5. The foregoing test for sufficient acidity is referenced elsewhere herein as "sodium bicarbonate test" and assumes sufficient passage of time for substantially complete dissolution of the pharmaceutical composition and intermixing thereof with the sodium bicarbonate solution. Enough acid to lower pH, in the sodium bicarbonate test, to about 2.8 may be used in some embodiments. Preferably at least 200 milligrams, and more preferably at least 300 milligrams (sometimes 400 milligrams) of the pH-lowering agent are used in the pharmaceutical composition of the invention. The foregoing preferences relate to the total combined weight of all pH-lowering agents where two or more of such agents are used in combination. The pharmaceutical composition of the invention should not include an amount of any base which, when released together with the pH-lowering compound, would prevent the pH of the above-described sodium bicarbonate test from dropping to 5.5 or below.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. It is preferred that at least one pH-lowering agent used in the invention have a pKa no higher than 4.2, and preferably no higher than 3.0. It is also preferred that the pH lowering agent have a solubility in water of at least 30 grams per 100 milliliters of water at room temperature. In some embodiments, organic acids are used.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof. Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Other useful pH-lowering agents that might not usually be called "acids" in the art, but which may nonetheless be useful in accordance with the invention are phosphate esters (e.g., fructose 1, 6 diphosphate, glucose 1, 6 diphosphate, phosphoglyceric acid, and diphosphoglyceric acid). CARBOPOL® (Trademark BF Goodrich) and polymers such as polycarbophil.

Any combination of pH lowering agents that achieves the required pH level of no higher than 5.5 in the sodium bicarbonate test discussed supra may be used. One preferred embodiment utilizes, as at least one of the pH-lowering agents of the pharmaceutical composition, an acid selected from the group consisting of citric acid, tartaric acid and an acid salt of an amino acid.

Regardless of the acid chosen, it is preferred to use acid particles coated with a protective coating discussed in a separate section, infra.

When salmon calcitonin is the peptide active agent, it is preferred that the weight ratio of pH-lowering agent to salmon calcitonin exceed 200:1, preferably 800:1 and most preferably 2000:1.

OPTIONAL COMPONENTS

As used herein, a component is considered "optional" if it is not required by one or more of the patent claims hereto.

Optional Water Soluble Barrier Layer

When a water soluble barrier layer is used, it is preferred that it be comprised of a compound that is water soluble in both acidic and basic environments. Examples of compounds useful for this purpose include but are not limited to hydroxypropylmethylcellulose, hydroxypropylcellulose, methylcellulose and polyvinylpyrolidone. Preferably, water solubility is at least one gram, more preferably at least 11 grams, per 100 milliliters at room temperature. Polyvinylpyrolidone is preferred in some embodiments. In some embodiments water solubility, at both pH 6.0 and pH 8.0, is in excess of 12 grams per 100 milliliters of water at room temperature. Good solubility in both acid and basic pH aids desirable quick dissolution in the intestinal region where pH is generally basic, but where the pharmaceutical composition's release of significant quantities of acid might at least temporarily impede dissolution of a material that was not also readily soluble in an aqueous acid environment. The water-soluble barrier layer is preferably used in embodiments wherein the composition includes an acid-resistant protective vehicle as its outer layer (for protecting the peptide active agent from stomach proteases). While the existence of such a vehicle does not require use of a water-soluble barrier layer, it is preferred to use one, preferably one that is non-ionic (to reduce undesirable interaction with the acid-protective vehicle). Preferably, the water-soluble barrier layer adds at least 3% to the weight of the pharmaceutical composition (exclusive of any acid-resistant protective vehicle), especially 3-6%. In some embodiments the amount of water soluble barrier exceeds the amount of acid-resistant protective vehicle.

Optional Coated Acid Particles

It is preferred that the acid be provided, at least in part, by acid particles coated with a protective coating to reduce undesirable acid interaction with other components of the formulation, such as the peptide active agent and, where used, the outer enteric coating. When coated acid particles are used, the particles are coated with a pharmaceutically acceptable protective coating that is non-acidic and preferably has a solubility in water of at least one gram, and preferably at least 10 grams, per 100 milliliters of water at room temperature. As the coating is for the purpose of reducing acid interaction with other components of the pharmaceutical composition, it is important that the coating not itself be acidic such that its own acidity could undesirably cause some of the acid interactions that it is the coating's purpose to prevent. Good water solubility is also important for quick dissolution, which in turn desirably aids a more simultaneous release of the pharmaceutical acid and the peptide active agent (and when optionally used, the absorption enhancer).

Appropriate coating materials include but are not limited to sugars (e.g. glucose), and acid salts (e.g. sodium citrate). When acid salts are used, it is preferred, but not required, that they be salts of the acid being coated (e.g., sodium citrate-coated citric acid particles). Preferred coated acid particles include but are not limited to glucose-coated citric acid particles available from Jungbunzlauer under the trademark CITROCOAT. When used as the acid, citric acid or other organic acids can be coated by spraying a coating solution which contains, for example, glucose or sodium citrate onto granules of an organic acid in a fluid-bed dryer. Coatings discussed herein may be used on particles of other acids discussed herein. Glucose-coated citric acid has proven to provide good dissolution properties as shown in Examples 1-3, infra.

Preferred average size of the acid-coated particles is from 30 mesh to 140 mesh.

Optional Absorption Enhancer

It is preferred that an absorption enhancer be included in the pharmaceutical composition. The absorption enhancers are preferably present in a quantity that constitutes from 0.1 to 20.0 percent by weight, relative to the overall weight of the pharmaceutical composition (exclusive of any enteric coating). Preferred absorption enhancers are surface active agents which act both as solubility enhancers and uptake enhancers. Generically speaking, "solubility enhancers" improve the ability of the components of the invention to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both functions. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent, aiding its passage into and through the intestinal mucus, (3) enhancing the ability of the normally polar peptide active agent to cross the epithelial barrier of the brush border membrane; and (4) increasing transcellular and/or paracellular transport as described above.

When surface active agents are used as the absorption enhancers, it is preferred that they be free flowing powders for facilitating the mixing and loading of capsules during the manufacturing process. Because of inherent characteristics of salmon calcitonin and other peptides (e.g., their isoelectric point, molecular weight, amino acid composition, etc.) certain surface active agents interact best with certain peptides. Indeed, some can undesireably interact with the charged portions of salmon calcitonin and prevent its absorption, thus undesireably resulting in decreased bioavailability. It is preferred, when trying to increase the bioavailability of salmon calcitonin or other peptides that any surface active agent used as an absorption enhancer be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. It is also preferred that the absorption enhancer be soluble at acid pH, particularly in the 3.0 to 5.0 range.

One especially preferred combination, when salmon calcitonin is the peptide active agent, is a mixture of cationic surface active agents and anionic surface active agents that are cholesterol derivatives, both of which are soluble at acid pH.

A particularly preferred combination is an acid soluble bile acid together with a cationic surface active agent. An acyl carnitine and sucrose ester is a good combination. When a particular absorption enhancer is used alone, it is preferred that it be a cationic surface active agent. Acyl carnitines (e.g., lauroyl carnitine), phospholipids and bile acids are particularly good absorption enhancers, especially acyl carnitine. Anionic surfactants that are cholesterol derivatives are also used in some embodiments. It is the intent of these preferences to avoid interactions with the peptide agent that interfere with absorption of peptide agent into the blood.

To reduce the likelihood of side effects, preferred detergents, when used as the absorption enhancers of the invention, are either biodegradable or reabsorbable (e.g. biologically recyclable compounds such as bile acids, phospholipids, and/or acyl carnitines), preferably biodegradable. Acyl carnitines are believed particularly useful in enhancing paracellular transport. When a bile acid (or another anionic detergent lacking linear hydrocarbons) is used in combination with a cationic detergent, salmon calcitonin is better transported both to and through the intestinal wall.

Preferred absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lysophospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc.

In some preferred embodiments, and without intending to be bound by theory, cationic ion exchange agents (e.g. detergents) are included to provide solubility enhancement by another possible mechanism. In particular, they may prevent the binding of salmon calcitonin or other peptide active agents to mucus. Preferred cationic ion exchange agents include protamine chloride or any other polycation.

Optional Acid-Resistant Protective Vehicle

It is preferred that an acid-resistant protective vehicle be utilized to separate the peptide active agent from stomach proteases. Any carrier or vehicle that protects the peptide from stomach proteases and then dissolves so that the other ingredients of the invention may be released in the intestine is suitable. Many such enteric coatings are known in the art, and are useful in accordance with the invention. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, the active peptide, absorption enhancers such as solubility and/or uptake enhancer(s) (when included), and pH-lowering agent(s), are included in a sufficiently viscous protective syrup to permit protected passage of the components of the invention through the stomach.

Suitable enteric coatings for protecting the peptide agent from stomach proteases may be applied, for example, to capsules after the remaining components of the invention have been loaded within the capsule. In other embodiments, enteric coating is coated on the outside of a tablet or coated on the outer surface of particles of active components which are then pressed into tablet form, or loaded into a capsule, which is itself preferably coated with an enteric coating.

It is very desirable that all components of the invention be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present invention is believed effective in the colon as well as in the small intestine. Numerous vehicles or carriers, in addition to the ones discussed above, are known in the art. It is desirable (especially in optimizing how simultaneously the components of the invention are released) to keep the amount of enteric coating low. Preferably, the enteric coating adds no more than 30% to the weight of the remainder of pharmaceutical composition (the "remainder" being the pharmaceutical composition exclusive of enteric coating itself). More preferably, it adds less than 20%, especially from 12% to 20% to the weight of the uncoated composition. The enteric coating preferably should be sufficient to prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute. In embodiments in which the water-soluble barrier layer of the invention is used, less enteric coating may be required, sometimes less that the amount of water-soluble barrier layer.

Optional Filler

It is preferred that a filler such as a cellulose filler like PROSOLV™ available from JRS Pharma be utilized. Other fillers are known in the art.

Optional Pharmaceutical Binder for Dry Compression

It is preferred that the pharmaceutical composition be in tablet form and that a pharmaceutical binder for dry compression be included in the pharmaceutical composition. Preferred binders include but are not limited to KOLLIDON VA64, KOLLIDON VA64 fine, KOLLIDON 30, AVICEL PH-101, PHARMACOAT 606, and MALDEX. The first three are commercially available from BASF, and the latter three are available from FMC Biopolymer, Shin-Etsu, and Amylum, respectively.

To improve simultaneous release, thorough intermixing of the components of the pharmaceutical composition (other than any optional enteric coating or barrier layer) results in substantially uniform dispersion of said components within the binder. For this purpose, coated acid particles (when used) are considered a single component. It is especially preferred that acid (or when used, coated acid particles) and peptide active agent be uniformly dispersed.

Optional Pharmaceutical Disintegrant

In some embodiments, a pharmaceutical tablet is used as a preferred dosage form. Preferably, a pharmaceutically acceptable disintegrant is included. Any disintegrant that performs the function of enhancing dissolution speed may be used. Preferred disintegrants include but are not limited to POLYPLASDONE, EXPLOTAB, and AC-DI-SOL, available from International Specialty Products, JRS Pharma and FMC Biopolymer, respectively. Preferably, the disintegrant is present in an amount between 1 and 15 percent by weight relative to the total tablet weight (when tablets are used), exclusive of any water-soluble barrier layer and any acid-resistant protective vehicle.

Optional Pharmaceutical Glidant

In preferred embodiments, a pharmaceutically acceptable glidant is included. Any glidant that performs the function of enhancing powder flow may be used. Preferred glidants include but are not limited to talc, calcium silicate, magnesium silicate, silicon dioxide. Preferably, the glidant is present in an amount between 0.1 and 2.0 percent by weight relative to the weight of the pharmaceutical composition, exclusive of any water-soluble barrier layer and any acid-resistant protective vehicle.

Optional Pharmaceutical Lubricant

In preferred embodiments, a pharmaceutically acceptable lubricant is included. Any lubricant that performs the function of preventing powder from sticking to the tooling may be used. Preferred lubricants include but are not limited to stearic acid, magnesium stearate, and hydrogenated vegetable oil type 1. Preferably, the lubricant is present in an amount between 0.5 and 5.0 percent by weight relative to the weight of the pharmaceutical composition, exclusive of any water-soluble barrier layer and any acid-resistant protective vehicle.

Optional Antioxidant

In some preferred embodiments, a pharmaceutically acceptable antioxidant is included. Any antioxidant that performs the function of preventing the oxidation of labile amino acids in peptides, such as methionine or tryptophan may be used. Preferred antioxidants include but are not limited to sodium pyruvate, derivatives of sodium pyruvate, ascorbic acid, ascorbyl palmitate, butylated hydroxyanisole, butylated hydroxytoluene, sodium bisulfite, and sodium metabisulfite. Preferably, the antioxidant is present in an amount between 0.5 and 5 mg per tablet.

Miscellaneous Other Optional Ingredients

In some preferred embodiments, another peptide (such as albumin, casein, soy protein, other animal or vegetable proteins and the like) is included to reduce non-specific adsorption (e.g., binding of peptide to the intestinal mucus barrier) thereby lowering the necessary concentration of the expensive peptide active agent. When added, the peptide is preferably from 1.0 to 10.0 percent by weight relative to the weight of the overall pharmaceutical composition (excluding any water-soluble barrier layer and any acid-resistant protective vehicle). Preferably, this second peptide is not physiologically active and is most preferably a food peptide such as soybean peptide or the like. Without intending to be bound by theory, this second peptide may also increase bioavailability by acting as a protease scavenger that desirably competes with the peptide active agent for protease interaction. The second peptide may also aid the active compound's passage through the liver.

All pharmaceutical compositions of the invention may optionally also include common pharmaceutical carriers, diluents or fillers. The compositions may include gelatin capsules, preservatives, colorants and the like in their usual known sizes and amounts.

The optional ingredients discussed herein is not exclusive. Other pharmaceutically acceptable agents may also be included. All optional components may be combined in any combination. Because most preferences stated herein provide benefits by different mechanisms, such combinations should be beneficial.

Other Optional Preferences

When prepared in tablet form, it is preferred that the maximum weight loss during friability testing be no greater than 1%. As used herein, friability testing refers to the technique described in "Tablet Friability", Chapter 1216, USP 28 page 2745.

When absorption enhancers are used, it is preferred that the weight ratio of pH-lowering agent(s) (exclusive of coating on any coated acid particles being used) to absorption enhancer(s) be between 3:1 and 20:1, preferably 4:1-12:1, and most preferably 5:1-10:1. The total weight of all pH-lowering agents and the total weight of all absorption enhancers in a given pharmaceutical composition is included in the foregoing preferred ratios. For example, if a pharmaceutical composition includes two pH-lowering agents and three absorption enhancers, the foregoing ratios will be computed on the total combined weight of both pH-lowering agents and the total combined weight of all three absorption enhancers.

It is preferred that the pH-lowering agent, the peptide active agent (and the absorption enhancer, when used) (whether single compounds or a plurality of compounds in each category) be uniformly dispersed in the pharmaceutical composition. In one embodiment, the pharmaceutical composition comprises granules that include a pharmaceutical binder having the peptide active agent, the pH-lowering agent and the absorption enhancer uniformly dispersed within said binder. In one embodiment, granules may consist of an acid core, surrounded by a uniform layer of organic acid, a layer of enhancer and a layer of peptide that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, optional absorption enhancers, and peptide active agents of the invention.

In one preferred embodiment, peptide, acid (preferably coated acid), absorption enhancer, a pharmaceutical binder (when necessary) for dry compression, a disintegrant, a glidant, a stabilizer (when necessary) and a lubricant are all used. Preferably, these materials are thoroughly intermixed, compressed into tablet form, coated with a water-soluble barrier layer (preferably adding at least 3% to the weight of the tablet (e.g. 3-6%), which is in turn coated with an enteric coating that adds another 4-10% to the weight of the tablet (e.g. 4-7%). In one preferred embodiment, the water soluble layer adds more than the enteric coating (e.g. 6% and 4%, respectively).

The invention is further illustrated by the following non-limiting examples.

Example 1

TABLE 1

Composition of Tablets

| | Non-coated Citric acid Tablet mg | Coated Citric Acid Tablet mg |
|---|---|---|
| Citric acid powder | 500 | 0 |
| Coated citric acid | 0 | 500 |
| Microcrystalline cellulose | 112 | 251 |
| Povidone | 25 | 40 |
| Crospovidone (disintegrant) | 49 | 9 |
| Talc | 7 | 0 |
| Magnesium stearate | 7 | 4 |

Granulated citric acid tablets were prepared by compressing citric acid that was fluid-bed granulated with citric acid powder, microcrystalline cellulose and povidone with crospovidene, talc and magnesium stearate. Coated citric acid tablets were prepared by compressing glucose-coated citric acid with microcrystalline cellulose, povidone, crospovidone and magnesium stearate.

The dissolution of tablets prepared from both types of citric acid was monitored by measuring the amount of citric acid released from each tablet in a USP dissolution vessel under standard conditions. The results in FIG. 1 show that tablets prepared from coated citric acid released their contents much more rapidly than tablets prepared from non-coated citric acid. Within 10 minutes nearly 60% of the coated acid tablet had dissolved whereas only 20% of the tablet prepared from non-coated citric acid had dissolved. By 30 minutes 100% of the tablet prepared from coated citric acid had dissolved, whereas the non-coated citric acid tablet required 60 minutes to completely dissolve.

Example 2

TABLE 2

Preferred Tablet Formulation

| Item | mg |
|---|---|
| sCT | .2-10 |
| Prosolv HD90 | 200 |
| Citric Acid DC F20 | 500 |
| Lauroyl-L-Carnitine* | 50 |
| Crospovidone | 9 |
| Kollidon VA64 | 40 |
| Sodium Pyruvate** | 1 |
| Magnesium Stearate | 4 |

*For tablets not containing Lauroyl-L-Carnitine add an additional 50 mg of Prosolv HD90.
**Sodium pyruvate included when using peptides that can undergo methionine oxidation.

Steps for Forming Tablet of Table 2
1. High shear or Comill geometrical mixing of peptide such as sCT and Prosolv.
2. Add mixed components of step 1 to V blender along with remaining components except magnesium stearate. Mix in V blender.
3. Add magnesium stearate to V blender after step 2 completed. Mix in V blender briefly.
4. Compress blend into tablets.
5. Coat tablets with subcoat to 6% weight gain.
6. Coat tablets with enteric coat to 7% weight gain.

Example 3

TABLE 3

Stability of Salmon Calcitonin in Tablets Prepared from Coated and Non-coated Citric Acid

| Weeks at Room Temperature | Coated Citric Acid | Non-coated Citric Acid |
|---|---|---|
| | Percent sCT Recovered | |
| 4 | 103 | 91 |
| 8 | 98 | 81 |
| 12 | 98 | Not determined |
| 24 | 95 | Not determined |
| 36 | 95 | Not determined |

Salmon calcitonin was dispersed in tablets prepared from either coated or non-coated citric acid, povidone, microcrystalline cellulose, talc and magnesium stearate. The tablets were stored at 4° centigrade and room temperature for up to 36 weeks. The sCT content was determined and is summarized in Table 3 as recovery of sCT from tablets stored at room temperature relative to tablets stored at 4° centigrade. The results in Table 3 show that there was a trend toward a progressive decrease in amount of sCT in tablets prepared from non-coated citric acid, whereas sCT was significantly more stable in tablets prepared from coated citric acid.

Example 4

TABLE 4

Effect of HPMC Undercoat on sCT Cmax

| HPMC Undercoat % tablet weight gain | L30D-55 Enteric coat | sCT Cmax pg/ml |
|---|---|---|
| 0 | 4 | 70 |
| 3 | 4 | 142 |
| 6 | 4 | 667 |
| 0 | 7 | 121 |
| 3 | 7 | 378 |
| 6 | 7 | 510 |

The indicated amount of hydroxypropylmethylcellulose (HPMC) was applied to tablets that were prepared by mixing salmon calcitonin (1.7 mg) coated citric acid (500 mg), microcrystalline cellulose (Prosolv, 251 mg), Kollidon VA64 fine (40 mg), Crospovidone (9 mg) and magnesium stearate (4 mg) in a V blender, followed by dry compression. Following application of the indicated amounts of HPMC to the indicated weight gain (in those examples utilizing the undercoat), the tablets were then sealed with an enteric coat made of Eudragit L30D-55 to the indicated further weight gain. Beagle dogs were given a tablet of the indicated combination of undercoat-enteric coat and aliquots of blood were taken at 15 minute intervals for 4 hours. Plasma was separated from the blood samples and analyzed for sCT by ELISA. The peak concentration (Cmax) of sCT for each combination undercoat-enteric coat is shown in Table 4. The results indicate that in the absence of an undercoat the Cmax of sCT increased 1.7 fold when the amount of enteric coat was increased nearly 1.75 fold. When an HPMC undercoat was included, the Cmax of sCT increased more than 9-fold in one embodiment, and substantially in all embodiments.

Example 5

TABLE 5

Effect of Sodium Pyruvate on PTH(1-31)$NH_2$ Stability and Recovery

| Sodium Pyruvate mg | PTH(1-31)$NH_2$ | | | |
|---|---|---|---|---|
| | Label claim | Purity Percent | Impurity 1 | Impurity 2 |
| 0 | 86.8 | 88.1 | 3.7 | 5.4 |
| 1 | 91.3 | 98.1 | 0.0 | 0.0 |

PTH(1-31)$NH_2$ (2 mg) and lauroyl-L-carnitine (50 mg) were dispersed in tablets prepared as described in Table 2 with and without 1 mg sodium pyruvate. The tablets were sealed with a non-ionic subcoat and an L30D-55 enteric coat. The PTH(1-31)$NH_2$ content of the tablets was analyzed following their manufacture. The results in Table 5 show that in the absence of sodium pyruvate there was significant oxidation of the peptide (impurities 1 and 2) and less than 90% recovery of the expected amount of PTH(1-31)$NH_2$. By contrast in the presence of a trace amount of sodium pyruvate there was no evidence of peptide degradation and recovery of PTH(1-31)$NH_2$ was greater than 90%.

Example 6

TABLE 6

Effect of Type of Subcoat on PTH(1-31)$NH_2$ Cmax in Dogs

| Subcoat | PTH(1-31)$NH_2$ Cmax pg/ml |
|---|---|
| Hydroxypropylmethylcellulose (HPMC) | 150 |
| Polyvinylpyrrolidone (PVP) | 328 |

PTH(1-31)$NH_2$ (2 mg) and lauroyl-L-carnitine (50 mg) were dispersed in tablets prepared as described in Table 2, sealed to a 6% weight gain with either an HPMC based subcoat or a PVP based subcoat and a 7% weight gain of L30D-55. Beagle dogs were given an enteric-coated tablet with either of the indicated types of subcoats and aliquots of blood were taken at 15 minute intervals for 4 hours. Plasma was separated from the blood samples and analyzed for PTH (1-31)$NH_2$ by ELISA. The results summarized in Table 6 show that PTH(1-31)$NH_2$ could be orally delivered to dogs and that there was a 2 fold improvement in plasma Cmax when the subcoat was made from PVP.

Treatment of Patients

When salmon calcitonin is chosen as active ingredient for treatment of osteoporosis, periodic administration is recommended. Salmon calcitonin is metabolized quickly with a half-life of only 20-40 minutes following subcutaneous administration in man. However, its beneficial effect on osteoclasts is much longer lasting, and may last for more than 24 hours notwithstanding rapid decrease in blood levels. There is usually no detectable blood levels more than two hours after injection of salmon calcitonin at conventional dosages. Accordingly, periodic administration of one dose about 5 days per week is preferred. Subcutaneous administration of salmon calcitonin (100 International units) has frequently resulted in peak serum concentration of about 250 picograms per milliliter. Nasally administered salmon calcitonin (200 International units) has proven effective against osteoporosis at peak levels as low as 10 picograms per milliliter. Some patients report certain side-effects such as flushing nausea etc. at high peak levels (e.g. at or above 200 picograms per milliliter). Accordingly, it is preferred that serum salmon calcitonin peak between 10 and 150 picograms per milliliter, more preferably between 10 and 50 picograms per milliliter. The serum levels may be measured by radioimmunoassay techniques known in the art. The attending physician may monitor patient response, salmon calcitonin blood levels, or surrogate markers of bone disease (such as serum CTX I, the C-terminal fragment of type 1 collagen breakdown), especially during the initial phase of treatment (1-6 months). He may then alter the dosage somewhat to account for individual patient metabolism and response.

The bioavailability achievable in accordance with the present invention is expected to permit oral delivery of salmon calcitonin into the blood at the above-identified preferred concentration levels while using only 100-1000 micrograms of salmon calcitonin per dosage form, preferably 100-400 micrograms, especially between 100 and 200 micrograms.

Regardless of the active agent being administered, it is preferred that a single dosage form (for example, a single capsule or tablet) be used at each administration because a single capsule or tablet best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is best achieved by administering all components of the invention as a single pill or capsule. However, the invention also includes, for example, dividing the required amount of all components among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. A single dosage form for oral delivery of a physiologically active peptide agent, comprising the active peptide agent intermixed with pharmaceutically acceptable acid particles that are coated with a pharmaceutically acceptable protective coating to separate the acid particles from the active peptide agent, wherein the protective coating has a solubility in water of at least one gram per 100 milliliters of water at room temperature, and wherein, if the dosage form were added to ten milliliters of 0.1 M aqueous sodium bicarbonate solution, the pH of the solution would be lowered to no higher than 5.5.

2. The single dosage form of claim 1 wherein the protective coating is maltodextrin.

3. The single dosage form of claim 1 wherein the protective coating is glucose.

4. The single dosage form of claim 1 wherein the protective coating is sodium citrate.

5. The single dosage form of claim 1 wherein the acid particles are maltodextrin-coated citric acid particles.

6. The single dosage form of claim 1 further comprising an absorption enhancer.

7. The single dosage form of claim 6 wherein the absorption enhancer is an acyl carnitine.

8. The single dosage form of claim 6 wherein the absorption enhancer is L-lauroyl carnitine.

9. The single dosage form of claim 1 wherein the acid has a pKa no higher than 4.2 and has a solubility in water of at least 30 grams per 100 milliliters of water at room temperature.

10. The single dosage form of claim 1 wherein the acid is selected from citric acid, tartaric acid and an acid salt of an amino acid.

11. The single dosage form of claim 6 further comprising a pharmaceutical binder and, uniformly dispersed in the binder, the acid particles, the absorption enhancer, and the peptide active agent.

12. The single dosage form of claim 1 wherein the active peptide is selected from calcitonin, natural parathyroid hormone, a parathyroid hormone truncate, and an amidated parathyroid hormone truncate.

13. The single dosage form of claim 1 wherein the active peptide is calcitonin.

14. The single dosage form of claim 1 wherein the active peptide is salmon calcitonin.

15. The single dosage form of claim 1 wherein the active peptide is PTH 1-31-amide.

16. The single dosage form of claim 1 further comprising a cellulose filler, wherein the single dosage form has been compressed into tablet form such that the maximum weight loss during friability testing is no greater than 1%.

17. The single dosage form of claim 1 further comprising a pharmaceutical binder for dry compression.

18. The single dosage form of claim 1 wherein average particle size of the coated acid particles is between 30 mesh and 140 mesh.

19. The single dosage form of claim 1 wherein the single dosage form composition is a single tablet or capsule.

20. A pharmaceutical tablet for oral delivery of a physiologically active peptide agent comprising:
    (A) the active peptide agent;
    (B) L-lauroyl carnitine;
    (C) coated citric acid particles intermixed with the active peptide agent, wherein the coating separates the citric acid from the active peptide agent in the composition, wherein total citric acid, exclusive of coating, exceeds 200 milligrams per tablet;
    (D) a cellulose filler;
    (E) a pharmaceutical binder for dry compression;
    (F) an outer layer of an acid-resistant enteric coating effective to transport the pharmaceutical tablet through the stomach of a patient while preventing contact between the active peptide agent and stomach proteases; and
    (G) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone and being present in an amount higher than three percent by weight relative to the total weight of the pharmaceutical tablet, exclusive of the outer layer and the barrier layer;

wherein, if the tablet were added to ten milliliters of 0.1 M aqueous sodium bicarbonate solution, the pH of the solution would be lowered to no higher than 5.5.

21. The pharmaceutical tablet of claim 20 wherein the coating is maltodextrin.

22. The pharmaceutical tablet of claim 20 wherein the average particle size of the coated citric acid particles is between 30 mesh and 140 mesh.

23. The pharmaceutical tablet of claim 20 wherein the peptide agent is selected from calcitonin, natural parathyroid hormone, a parathyroid hormone truncate, and an amidated parathyroid hormone truncate.

24. The pharmaceutical tablet of claim 20 wherein the active peptide is calcitonin.

25. The pharmaceutical tablet of claim 20 wherein the active peptide is salmon calcitonin.

26. The pharmaceutical tablet of claim 20 wherein the active peptide is PTH 1-31-amide.

27. A pharmaceutical tablet for oral delivery of a physiologically active peptide agent comprising:
    (A) the active peptide agent;
    (B) L-lauroyl carnitine;
    (C) coated citric acid particles intermixed with the active peptide agent, wherein the coating separates the citric acid from the active peptide agent in the composition, wherein total citric acid, exclusive of coating, exceeds 200 milligrams per tablet;
    (D) a cellulose filler;
    (E) a pharmaceutical binder for dry compression;
    (F) an outer layer of an acid-resistant enteric coating effective to transport the pharmaceutical tablet through the stomach of a patient while preventing contact between the active peptide agent and stomach proteases; and
    (G) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical, exclusive of the outer layer and the barrier layer, wherein the tablet has been compressed into tablet form such that the maximum weight loss during friability testing is no greater than 1%, and wherein the tablet reduces the activity of neutral to basic-acting proteases upon dissolution in the small intestine by reducing intestinal pH.

28. A pharmaceutical tablet for oral delivery of calcitonin comprising:
    (A) calcitonin;
    (B) a lauroyl carnitine absorption enhancer;
    (C) coated citric acid particles intermixed with the calcitonin, wherein the coating separates the citric acid from the calcitonin, wherein total citric acid, exclusive of coating, exceeds 200 milligrams per tablet;
    (D) a cellulose filler;
    (E) a pharmaceutical binder for dry compression;
    (F) an outer layer of an acid-resistant enteric coating effective to transport the pharmaceutical tablet through the stomach of a patient while preventing contact between the active peptide agent and stomach proteases; and
    (G) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical tablet, exclusive of the outer layer and the barrier layer;

wherein the tablet has been compressed into tablet form such that the maximum weight loss during friability testing is no greater than 1%; and wherein, if the tablet were added to ten milliliters of 0.1 M aqueous sodium bicarbonate solution, the pH of the solution would be lowered to no higher than 5.5.

29. The pharmaceutical tablet of claim 28 wherein the calcitonin is salmon calcitonin.

30. The pharmaceutical tablet of claim 28 wherein the coating is maltodextrin.

31. A single dosage form for oral delivery of an amidated parathyroid hormone truncate comprising the amidated parathyroid hormone truncate intermixed with pharmaceutically acceptable acid particles that are coated with a pharmaceutically acceptable protective coating to separate the acid particles from the amidated parathyroid hormone truncate, wherein the protective coating has a solubility in water of at least one gram per 100 milliliters of water at room temperature, and wherein, if the dosage form were added to ten milliliters of 0.1 M aqueous sodium bicarbonate solution, the pH of the solution would be lowered to no higher than 5.5.

32. The single dosage form of claim 31 wherein the protective coating is maltodextrin.

33. The single dosage form of claim 31 wherein the protective coating is sodium citrate.

34. The single dosage form of claim 31 wherein the acid particles are maltodextrin-coated citric acid particles.

35. The single dosage form of claim 31 further comprising an absorption enhancer.

36. The single dosage form of claim 35 wherein the absorption enhancer is an acyl carnitine.

37. The single dosage form of claim 35, wherein the absorption enhancer is L-lauroyl carnitine.

38. The single dosage form of claim 31, wherein the acid is selected from citric acid, tartaric acid and an acid salt of an amino acid.

39. The single dosage form of claim 35, wherein the single dosage form further comprises a pharmaceutical binder and, uniformly dispersed in the binder, the acid particles, the absorption enhancer, and the amidated parathyroid hormone truncate.

40. A single dosage form for oral delivery of a physiologically active peptide agent, comprising the active peptide agent intermixed with pharmaceutically acceptable citric acid particles that are coated with a pharmaceutically acceptable protective coating to separate the citric acid particles from the active peptide agent, wherein the protective coating has a solubility in water of at least one gram per 100 milliliters of water at room temperature, and wherein, if the dosage form were added to ten milliliters of 0.1 M aqueous sodium bicarbonate solution, the pH of the solution would be lowered to no higher than 5.5.

41. The single dosage form of claim 40 wherein the protective coating is maltodextrin.

42. The single dosage form of claim 40 wherein the protective coating is sodium citrate.

43. The single dosage form of claim 40 wherein the citric acid particles are maltodextrin-coated citric acid.

44. The single dosage form of claim 40 further comprising an absorption enhancer.

45. The single dosage form of claim 44 wherein the absorption enhancer is a surface active agent.

46. The single dosage form of claim 44 wherein the absorption enhancer is an acyl carnitine.

47. The single dosage form of claim 44 wherein the absorption enhancer is L-lauroyl carnitine.

48. The single dosage form of claim 44 wherein the single dosage form further comprises a pharmaceutical binder and, uniformly dispersed in the binder, the citric acid particles, the absorption enhancer, and the peptide active agent.

49. The single dosage form of claim 40 wherein the active peptide is selected from calcitonin, natural parathyroid hormone, a parathyroid hormone truncate, and an amidated parathyroid hormone truncate.

50. The single dosage form of claim 40 wherein the active peptide is calcitonin.

51. The single dosage form of claim 40 wherein the active peptide is salmon calcitonin.

52. The single dosage form of claim 40 wherein the active peptide is PTH 1-31-amide.

53. A single dosage form for oral delivery of an amidated parathyroid hormone truncate comprising the amidated parathyroid hormone truncate intermixed with coated citric acid particles so as to separate the citric acid particles from the amidated parathyroid hormone truncate, wherein the protective coating has a solubility in water of at least one gram per 100 milliliters of water at room temperature, and wherein, if the dosage form were added to ten milliliters of 0.1 M aqueous sodium bicarbonate solution, the pH of the solution would be lowered to no higher than 5.5.

54. The single dosage form of claim 53 further comprising an absorption enhancer.

55. The single dosage form of claim 54 wherein the absorption enhancer is L-lauroyl carnitine.

56. The single dosage form of claim 53 wherein the dosage form is a single tablet or capsule.

57. A single dosage form for oral delivery comprising:
a physiologically active peptide agent;
pharmaceutically acceptable acid particles that are coated with a pharmaceutically acceptable protective coating to separate the acid particles from the physiologically active peptide agent; and
an absorption enhancer, wherein the dosage form reduces the activity of neutral to basic-acting proteases upon dissolution in the small intestine by reducing intestinal pH, wherein the protective coating has a solubility in water of at least one gram per 100 milliliters of water at room temperature, and wherein, if the dosage form were added to ten milliliters of 0.1 M aqueous sodium bicarbonate solution, the pH of the solution would be lowered to no higher than 5.5.

58. The single dosage form of claim 57 wherein the protective coating is maltodextrin.

59. The single dosage form of claim 57 wherein the absorption enhancer is a surface active agent.

60. The single dosage form of claim 57 wherein the absorption enhancer is an acyl carnitine.

61. The single dosage form of claim 57 wherein the absorption enhancer is L-lauroyl carnitine.

62. The single dosage form of claim 57 wherein the acid is selected from citric acid, tartaric acid and an acid salt of an amino acid.

63. The single dosage form of claim 57 wherein the active peptide is selected from calcitonin, natural parathyroid hormone, a parathyroid hormone truncate, and an amidated parathyroid hormone truncate.

64. The single dosage form of claim 57 wherein the composition is a single tablet or capsule.

65. The single dosage form of claim 57 wherein the active peptide is calcitonin.

66. The single dosage form of claim 57 wherein the active peptide is salmon calcitonin.

67. A pharmaceutical tablet for oral delivery of a physiologically active peptide agent comprising:
(A) the active peptide agent;
(B) coated citric acid particles intermixed with the active peptide agent, wherein the coating separates the citric acid from the active peptide agent, wherein total citric acid, exclusive of coating, exceeds 200 milligrams per tablet;
(C) a cellulose filler;
(D) a pharmaceutical binder for dry compression;
(E) an outer layer of an acid-resistant enteric coating effective to transport the single dosage form through the stomach of a patient while preventing contact between the active peptide agent and stomach proteases; and
(F) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone and being present in an amount higher than three percent by weight relative to the total weight of the single dosage form, exclusive of the outer layer and the barrier layer;
wherein, if the tablet composition were added to ten milliliters of 0.1 M aqueous sodium bicarbonate solution, the pH of the solution would be lowered to no higher than 5.5.

68. The pharmaceutical tablet of claim 67 wherein the coating is maltodextrin.

69. The pharmaceutical tablet of claim 67 wherein the average particle size of the coated citric acid particles is between 30 mesh and 140 mesh.

70. The pharmaceutical tablet of claim 67 wherein the active peptide agent is calcitonin 71. The pharmaceutical tablet of claim 67 wherein the active peptide agent is salmon calcitonin 72. A pharmaceutical tablet for oral delivery of a physiologically active peptide agent comprising:
(A) the active peptide agent;
(B) coated citric acid particles intermixed with the active peptide agent, wherein the coating separates the citric acid from the active peptide agent, wherein total citric acid, exclusive of coating, exceeds 200 milligrams per tablet;
(C) a cellulose filler;
(D) a pharmaceutical binder for dry compression;
(E) an outer layer of an acid-resistant enteric coating effective to transport the pharmaceutical tablet through the stomach of a patient while preventing contact between the active peptide agent and stomach proteases; and
(F) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical tablet, exclusive of the outer layer and the barrier layer,
wherein the tablet has been compressed into tablet form such that the maximum weight loss during friability testing is no greater than 1%, and
wherein the tablet reduces the activity of neutral to basic-acting proteases upon dissolution in the small intestine by reducing intestinal pH.

73. A pharmaceutical tablet for oral delivery of calcitonin comprising:
(A) calcitonin;
(B) coated citric acid particles intermixed with the calcitonin, wherein the coating separates the citric acid from the calcitonin, wherein total citric acid, exclusive of coating, exceeds 200 milligrams per tablet;
(C) a cellulose filler;
(D) a pharmaceutical binder for dry compression;
(E) an outer layer of an acid-resistant enteric coating effective to transport the pharmaceutical tablet through the stomach of a patient while preventing contact between the active peptide agent and stomach proteases; and
(F) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical tablet, exclusive of the outer layer and the barrier layer;
wherein the tablet has been compressed into tablet form such that the maximum weight loss during friability testing is no greater than 1%; and
wherein, if the tablet composition were added to ten milliliters of 0.1 M aqueous sodium bicarbonate solution, the pH of the solution would be lowered to no higher than 5.5.

74. The pharmaceutical tablet of claim 73 wherein the average particle size of the coated citric acid particles is between 30 mesh and 140 mesh.

75. The pharmaceutical tablet of claim 73 wherein the calcitonin is salmon calcitonin.

76. The pharmaceutical tablet of claim 73 wherein the coating is maltodextrin.

77. A pharmaceutical composition for oral delivery of a physiologically active peptide agent comprising said active peptide agent intermixed with pharmaceutically acceptable citric acid particles that are coated with maltodextrin to separate the citric acid particles from the active peptide agent in the composition.

78. The pharmaceutical composition of claim 77 further comprising an absorption enhancer.

79. The pharmaceutical composition of claim 78 wherein the absorption enhancer is L-lauroyl carnitine.

80. The pharmaceutical composition of claim 77 wherein the active peptide agent is selected from calcitonin, natural parathyroid hormone, a parathyroid hormone truncate, an amidated parathyroid hormone truncate, glucagon-like peptide-1 (GLP-1), desmopressin (DDAVP), leuprolide, 2,6-dimethyltyrosine-D-arginine-phenylalanine-lysine amide (DMT-DALDA) and analogs thereof.

81. The pharmaceutical composition of claim 77 wherein the active peptide agent is calcitonin.

82. The pharmaceutical composition of claim 77 wherein the active peptide agent is salmon calcitonin.

83. The pharmaceutical composition of claim 77 wherein the pharmaceutical composition is a single tablet or capsule.

* * * * *

UNITED STATES PATENT AND TRADEMARK OFFICE
CERTIFICATE OF CORRECTION

| | | |
|---|---|---|
| PATENT NO. | : 8,377,863 B2 | Page 1 of 1 |
| APPLICATION NO. | : 12/128210 | |
| DATED | : February 19, 2013 | |
| INVENTOR(S) | : Stern et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this
Sixteenth Day of December, 2014

Michelle K. Lee
*Deputy Director of the United States Patent and Trademark Office*